(12) United States Patent
Dunlop et al.

(10) Patent No.: US 10,632,130 B2
(45) Date of Patent: Apr. 28, 2020

(54) DEHYDROANDROSTEROL AND METHODS OF USING THE SAME

(71) Applicant: ACCELERATED GENETIX, LLC, Austin, TX (US)

(72) Inventors: John Dunlop, San Antonio, TX (US); Dongdong Chen, Shanghai (CN)

( * ) Notice: Subject to any disclaimer, the term of this patent is extended or adjusted under 35 U.S.C. 154(b) by 373 days.

(21) Appl. No.: 15/706,341

(22) Filed: Sep. 15, 2017

(65) Prior Publication Data

US 2018/0071314 A1    Mar. 15, 2018

Related U.S. Application Data

(60) Provisional application No. 62/395,124, filed on Sep. 15, 2016.

(51) Int. Cl.
| | |
|---|---|
| *A61K 31/5685* | (2006.01) |
| *A61P 5/26* | (2006.01) |
| *A61P 21/06* | (2006.01) |
| *A61K 9/14* | (2006.01) |
| *A61K 9/00* | (2006.01) |
| *A61K 31/568* | (2006.01) |
| *A61K 45/06* | (2006.01) |
| *A61P 15/00* | (2006.01) |
| *A61P 5/00* | (2006.01) |

(52) U.S. Cl.
CPC ........ *A61K 31/5685* (2013.01); *A61K 9/0053* (2013.01); *A61K 9/141* (2013.01); *A61K 31/568* (2013.01); *A61K 45/06* (2013.01); *A61P 5/00* (2018.01); *A61P 5/26* (2018.01); *A61P 15/00* (2018.01); *A61P 21/06* (2018.01); *A61K 2300/00* (2013.01)

(58) Field of Classification Search
CPC ... A61K 31/5685; A61K 2300/00; A61P 5/26; A61P 21/06
See application file for complete search history.

(56) References Cited

U.S. PATENT DOCUMENTS

2003/0119800 A1*  6/2003  Manolagas .......... A61K 31/045
                                                           514/178

* cited by examiner

*Primary Examiner* — Theodore R. West
(74) *Attorney, Agent, or Firm* — Benjamin Diederich

(57) ABSTRACT

A method of promoting muscle growth consisting of providing a dietary supplement containing an effective amount of dehydroandrosterol to a user. A composition for promoting muscle growth containing an effective amount of dehydroandrosterol.

13 Claims, 1 Drawing Sheet

DEHYDROANDROSTEROL AND METHODS OF USING THE SAME

CROSS-REFERENCE TO RELATED APPLICATIONS

This application claims the benefit of U.S. Provisional Application No. 62/395,124, filed on Sep. 15, 2016, the teachings of which are expressly incorporated by reference.

STATEMENT RE: FEDERALLY SPONSORED RESEARCH/DEVELOPMENT

Not Applicable

BACKGROUND

The present disclosure relates generally to a dietary supplement which stimulates androgenic and anabolic expressions, more particularly to a dietary supplement containing an endogenous, androgenic corticoid metabolite, and even more particularly to a dietary supplement containing dehydroandrosterol that promotes muscle growth.

It is well known that a person's diet affects their good health and quality of life. It is important to intake the necessary nutrients for a healthy lifestyle. While a person's diet generally determines which nutrients they acquire, dietary supplements may be consumed to supplement nutrients lacking in a person's diet. Dietary supplements are food products that supply nutrients that may be missing or not consumed in sufficient quantity. The food product may include one or more of a vitamin, mineral, herb or other botanical, or an amino acid. The food product can also include a dietary substance to supplement the diet by increasing a person's total dietary intake. More information regarding dietary supplements can be found in the Dietary Supplement Health and Education Act of 1994.

In general, the nutrients a person requires depends on many different factors, such as their activity level. Some people need and benefit from nutrients that stimulate the release of hormones. A hormone is a substance produced by one tissue and conveyed by the bloodstream to another tissue. Hormones are capable of spurring physiological activity, such as growth or metabolism. Corticoids are a particular class of hormones occurring in nature, especially as a product of the adrenal cortex. Corticoids are useful for a variety of applications, and some possess unique androgenic potential capable of promoting muscle growth and other characteristic effects. However, many of them have undesirable side effects as well.

For example, some anabolic androgenic steroids are man-made substances related to male sex hormones. The term "anabolic" generally refers to muscle-building, and the term "androgenic" generally refers to increased masculine-type characteristics. The term "steroids" generally refers to a class of drugs used to treat conditions that occur when the body produces abnormally low amounts of testosterone. Steroids are also used to treat body wasting in patients with diseases that result in loss of lean muscle mass. Abuse of anabolic steroids, however, can lead to serious health problems, and some of these health problems can potentially be irreversible.

Some of the potential health problems from ingesting anabolic androgenic steroids may include liver tumors and cancer, jaundice, fluid retention, high blood pressure, immune dysfunction, and adversely altered lipid metabolism. Other health problems include kidney tumors, severe acne, and trembling. In addition, there are some gender specific health problems that may occur, such as testicular atrophy, reduced sperm count, infertility, baldness, gynecomastia, and an increased risk for prostate cancer in men. For women, the health problems include the growth of facial hair, pattern baldness, and changes in or cessation of the menstrual cycle.

As can be understood, it is desirable to stimulate androgenic-anabolic expressions, including, but not limited to, muscle growth, without overt risk of undesirable health consequences.

Additionally, many steroid hormones are regulated by public law or private contract, thus greatly limiting the acceptable options for many potential consumers. Current regulations are viewed by many consumers as restrictive. Thus, these consumers are often tempted to pursue clandestine products in spite of the health risks and legal restrictions.

As such, there is a need for effective, legally acceptable alternatives in the natural market. The compositions and methods described herein offer androgenic and anabolic activity to a user, with no documented toxicity, are compliant with food supplement regulations, and are unscheduled by any current drug regulation. Thus, these compositions help to foster responsible consumer use by offering a natural and legal alternative to the dangerous, clandestine products that are otherwise being used and have become so prevalent.

BRIEF SUMMARY

The present disclosure describes compositions, dietary food supplements, and methods for achieving androgenic effects such as muscle growth, by utilizing an effective amount of DHA.

In accordance with one embodiment of the present disclosure, there is contemplated a method of stimulating androgenic expression in a user in need of said androgenic expression. The method includes providing to the user a composition having an effective amount of dehydroandrosterol. The stimulated androgenic expression may result in muscle growth of the user.

The composition may further include at least one ester, ether, or salt of dehydroandrosterol, or a combination thereof. Additionally, or alternatively, the composition may further include at least one isomer, stereoisomer, or isostere of dehydroandrosterol, or a combination thereof. The composition may include more than one form of dehydroandrosterol.

The composition may further include a carrier which carries the dehydroandrosterol. In particular, the carrier may be a solid, a liquid, or a combination thereof. The carrier may be shaped and dimensioned to facilitate its oral ingestion.

Under this method, the composition may be provided to the user on a regular basis, such as at least once every other day, or daily. In certain embodiments, the composition may be provided to the user such that the user receives between approximately 10 mg and approximately 400 mg of dehydroandrosterol daily.

The composition may further include an absorption enhancing agent. An exemplary agent may be a half-life enhancing agent.

Additionally, the composition may further include a second steroid other than dehydroandrosterol. For example, the second steroid may be androsterone. When a second steroid is contained within the composition, the relative amount of dehydroandrosterol and androsterone in the composition may be between approximately 1:4 and approximately 1:100.

In accordance with another embodiment of the present disclosure, there is contemplated a composition capable of stimulating androgenic expression in a user. The composition includes an effective amount of dehydroandrosterol. In particular, the composition may include more than one compositional form of dehydroandrosterol.

The composition may include a second (or even more than two) steroid component. In a certain embodiment, the second steroid component may be androsterone and the composition may contain a relative amount of dehydroandrosterol and androsterone between approximately 1:4 and approximately 1:100.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 1:
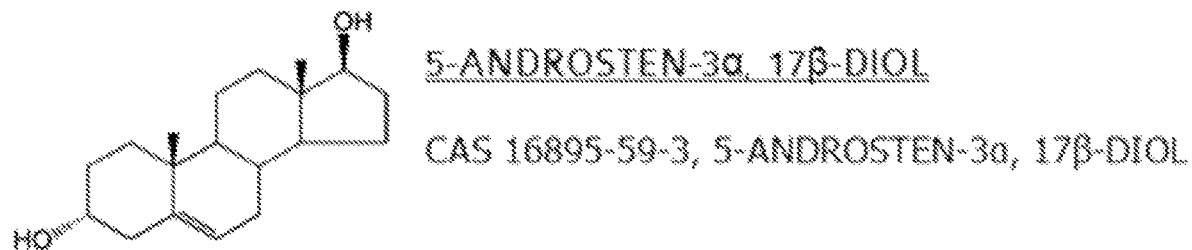
FIG. 1 is a skeletal formula of dehydroandrosterol (otherwise known as 5-androsten-3a, 1713-diol)

One embodiment of the present disclosure comprises a composition or dietary supplement which includes an effective amount of dehydroandrosterol (hereinafter referred to as DHA), and methods of using compositions or dietary supplements containing DHA to increase muscle growth. FIG. 1 shows a skeletal representation of DHA. An effective amount of DHA depends on many different factors, such as the person's weight and activity level. In general, however, the effective amount of DHA provides muscle growth. It should be noted that the muscle growth is generally in a human; however, the compositions and methods described herein can also be used to provide muscle growth in other mammals.

An effective amount of DHA in humans is believed to be between about 10 mg to about 300 mg, but the effective amount can be outside of this range for particular applications. For example, in some situations, the effective amount of DHA is between about 25 mg to about 75 mg. In one particular example, the effective amount of DHA is between about 50 mg to about 100 mg. In another example, the effective amount of DHA is between about 250 mg to about 400 mg. Additionally, less than 10 mg of DHA may be used, particularly when combined with other synergistic biological hormones. It should be noted that the effective amount of DHA is generally taken within a particular time period, for example, daily. However, the effective amount of DHA can be taken within other time periods, such as every other day, for example.

Figure 2:
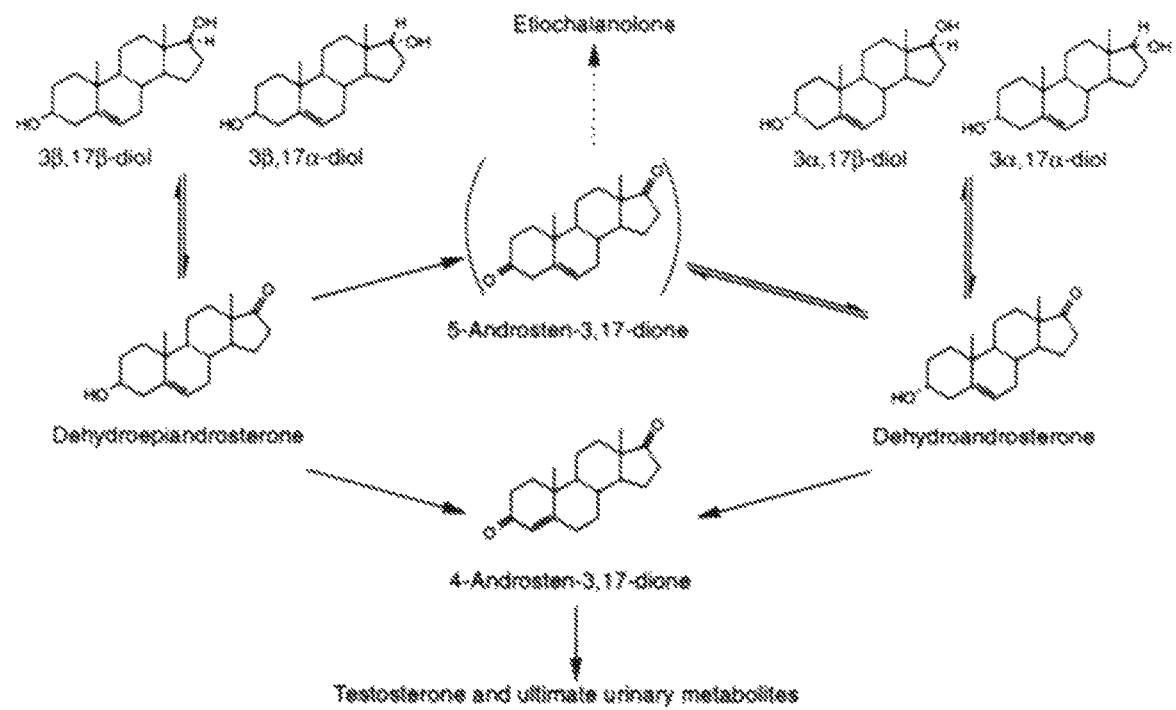
FIG. 2 is a diagram of the metabolic pathway in which dehydroandrosterol is biosynthesized in man.

As shown in FIG. 2, DHA is naturally biosynthesized in man with the primary adrenal substrate being dehydroandrosterone via 5-5-Androsten-3,17-dione via dehydroepiandrosterone. DHA has numerous synonyms, including, 5-Androsten-3a,17b-diol; Δ5-Androsten-3a,17b-diol; Androst-5-en-3a,17b-diol; Androst-5-ene-3,17-diol, (3a, 17b)-; Androst-5-ene-3a,17b-diol (8CI); and 3a,17b-Dihydroxyandrost-5-ene. Furthermore, DHA may be obtained in many different ways. For example, it can be synthesized from many animal steroid or plant sterols, or extracted intact or modified from the adrenal glands or urine of animals producing Δ5-steroids. DHA may also be a product of some botanicals.

DHA is an androgenic corticoid compound documented to occur and be active in man and animal and is estimated to possess relative androgenic activity equivalent to approximately 43% that of testosterone; testosterone being the conventional, comparative standard. Androgens primarily promotes muscle-building and increases masculine characteristics. DHA is a corticoid having androgenic activity which demonstrates anabolic, androgenic, anti-estrogenic, and anti-cortisol effects. DHA is believed to operate by attaching itself to androgen receptors of a muscle and, in response, the corresponding muscle grows. DHA causes an increase in lean muscle mass through its myotrophic action by increasing nitrogen retention and protein synthesis. DHA provides corticometric activity because it behaves as an anti-catabolic in response to its structure, so it reduces muscle catabolism.

The effective amount of DHA may include DHA in other compositional forms. For example, it can include an ester or esters, ether or ethers, salt or salts, and/or any combination of the aforementioned of DHA. It can also include an isomer, stereoisomer, or isostere of DHA. The supplement is ingested orally, so its size and shape is chosen to facilitate oral ingestion. The food product can be in the form of a pill, tablet, capsule, etc. The supplement can also be in the form of a powder, so it can be combined with a liquid carrier.

The DHA may be contained within a carrier, wherein the carrier may be a solid or liquid. The role of the carrier is to facilitate the administration of the dosage of DHA. A suitable concentration is, for example, about 10 mg to about 10 g of DHA per 100 g of carrier. The carrier can be in many different forms, such as a solid or liquid. When the carrier is a solid, it can be in the form of a pill, capsule, tablet, soft-gel, pearl, caplet, and other forms known within the art. There are many different sizes and shapes that can be used, such as those normally used for orally ingested medicaments. Since the composition is preferably ingested orally, its size and shape may be chosen to facilitate oral ingestion. The composition may also be in the form of a powder, so it can be later combined with a liquid carrier prior to use. The composition is ingested when it is taken orally into the body through the mouth so it can be digested. It is then converted in the alimentary canal into an absorbable form for assimilation into the body.

In some embodiments, the composition can include an absorption enhancing component. The absorption enhancing component may be of any useful type. In some embodiments, the composition includes a half-life enhancing component, which increases the amount of time the DHA, or another compositional form thereof, remains in the body. The half-life enhancing component can be of any useful type relative to various product specifications.

Human Clinical Pre-Trial Evaluation (Alpha Testing)

Two human, male volunteers were selected to pre-trial the DHA material by single daily oral administration. Both were of mature age, not naive to various exogenously supplied androgens, and in good general health. Food and exercise routine was not modified from normal during the testing period, so as to avoid introduction of confounding variables.

Both test subjects noted subjective improvements, as defined by weight, strength, and/or muscle hardness gain over a one month testing period. Doses were ramped 50 mg weekly, beginning at 50 mg and concluding at 200 mg.

One of the test subjects (Subject #2) took a two week washout after this initial testing regiment and resumed testing at 100 mg, ramping the dose weekly as prior but using 100 mg increments, such that at four weeks of testing the subject was using 400 mg.

After another two week washout period, Subject #2 elected to resume testing of DHA with another related compound, androsterone, at various doses. Over several more months, this DHA/androsterone ratio was altered over a range and maintained at various ratios for not less than five days at a time before modification. Subject #2 had the observatory goal of establishing synergistic optimization of ratios, and concluded an effective combination range between 1:4 and 1:100 for DHA/androsterone synergism.

Administration of exogenous hormones is not uncommonly accompanied by characteristic side-effects, generally proportional to the intrinsic character of the hormone, it's relative strength, receptor binding affinity, and the dose applied. These side effects include gynecomastia, dermatitis, reduction of testicular size and ejaculatory volume, alopecia, increased aggression, etc., and relate to the androgenic potential of the compound in question. Unexpectedly, both test subjects noted a lack of these side-effects, with mild acne being the only undesirable effect and only noted at the higher doses tested.

Both test subjects also experienced distinct improvements in the parameters associated with enhanced androgen status, such as increased muscle hardness/fullness and strength improvements uncharacteristic of typical gains within the time frame of testing. Effects appear to be proportional to dose in a fairly linear fashion.

Subject #2 engaged in the extended testing also noted punctuated androgenic synergism with androsterone over a wide dose range. This synergistic phenomenon had not been previously demonstrated with DHA. Delta-5 adrenal steroids such as DHA are often shown to possess synergism with other endogenous steroids, sometimes referred to as "biological amplification". The possible, biological utility of such interactions are apparent, but the precise mechanisms involved are not known absolutely. The synergistic enhancement is speculated to involve enzymatic processes between Delta-5 steroids (adrenal products like DHA and DHEA) and other sex steroids such as ring-reduced Androsterone and Delta-4 Testosterones. This synergistic mechanism affords an excellent means of utilizing lower doses of hormones to greater effect, and may explain the relative lack of side-effects encountered with DHA supplementation. Although DHA has been shown to possess considerable androgenic activity when assayed alone, its greatest contribution at lower doses may more likely be related to its enhancement of pre-existing endogenous or co-administered steroids.

Animal Clinical Pre-Trial Evaluation

Caprine studies were also performed in two test animals. The test animals selected were monozygous male twins, castrated and placed in separate pens not later than six weeks after birth.

At approximately three months of age, one of these two goats was selected to receive daily DHA in a single, bolus, oral dose. The other goat was not given DHA, and served as the control. All parameters were equalized (pen size, ambient temperature, once daily exercise for 15 minutes on tread mill, 30 minute "play" time with other goats, twice daily ad-lib feeding of identical source feed, etc.)

Dosing was initiated in the test goat at 50 mg. After two weeks, the dose was increased to 100 mg, then after another two weeks increased to 200 mg, then maintained at that dose for an additional four weeks.

At the end of the eight week testing period, the two test animals were weighed to establish gains made from their original base-line weight at the beginning of the study.

Both goats began the study at 46 pounds. At the end of testing, the control goat weighed 61 pounds, indicating a 33% general weight gain. This was considered to be within the normal rate range of development as per the opinions of the experienced pen managers in charge of housing the goats. However, the DHA test goat's weight increased from 46 to 73 pounds during the same test period, indicating a 59% general weight gain. The goat on the DHA regimen demonstrated greater appetite and food intake, and subsequently experienced weight gain approximately double that of the control goat. The weight gain of the test goat exceeded standards for statistical significance over the control, establishing a positive correlation between enhanced weight gain and DHA supplementation.

It had been anticipated that exogenously supplied androgen replacement, especially at higher doses, may reinstate typical, male behaviors such as bucking and mounting in castrate males. Alpha-male behavior was indeed noted to be established in the test goat when placed in the play pen with superior goats. This was manifest by the test goat challenging two larger goats with pre-established social hierarchy that were housed at the same facility.

Additionally, the pen manager in charge of the test goat noted another, unexpected observation, related to the behavioral demeanor of the animal. The test goat was observed to become unusually compliant and friendly toward all visiting humans and pen personnel. The pen manager mentioned that most goats protest the daily tread mill exercise in a predictable manner, and also tend to leave a portion of their daily food rations uneaten. However, the test goat became very "well behaved" once the dose reached 100-200 mg per day, happily engaging in forced exercise and eating all or more of the typically supplied rations.

It is unclear why DHA induced such pronounced behavioral improvement in the higher-dose caprine model, but, even at lower doses, supplementation demonstrates physical improvements in a trend similar to that noted by the human test subjects. It seems likely that the majority of weight gain associated with DHA use could be accounted for by lean muscle increase, based on the knowledge of DHA's biological activity and the observations of its subjective results upon supplementation.

Human Clinical Trial Evaluation (Beta Testing)

Two human, male volunteers were selected to trial the encapsulated DHA material by daily oral administration. They were allowed to select their own serving schedules and serving sizes (within reason of extrapolated values), provided they be consistent and document the compliance of their regimens. Both were of mature age, not naive to various exogenously supplied androgens, and in good general health. Food and exercise routine was not modified from normal during the testing period, so as to avoid introduction of confounding variables.

Both test subjects noted subjective and objective improvements, as defined by weight, strength, and/or muscle hardness gain over their testing respective periods. A summary of these results is noted below, and all capsules used contained 20 mg each of DHA. In particular, Trial Participant #1 was a 23 year old male who took five capsules a day (100 mg/day DHA) of the composition for sixteen weeks. At the end of this trial, this Participant #1 had gained fifteen pounds and improved his single repetition leg squats from 430 pounds at the beginning to 545 pounds at the end, deadlift from 455 pounds at the beginning to 560 pounds at the end, and bench press from 270 pounds at the beginning to 340 at the end. Trial Participant #2 was a 22 year old male who took four capsules a day (80 mg/day DHA) of the composition for six weeks. At the end of this trial, this Participant #2 had gained twelve pounds and improved all major lifting measurements by 20-25 pounds from start to finish.

Further results from consumer use has shown reported increases in strength, lean muscle gains, increased fat loss, appetite increase, libido boost, increased energy, and increased muscle hardness, with the only reported side effects being slight acne and slight lethargy.

The above description is given by way of example, and not limitation. Given the above disclosure, one skilled in the art could devise variations that are within the scope and spirit of the invention disclosed herein, including various ways of dosing the composition and carriers for providing the composition to users. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of effecting muscle growth in a user in need of said muscle growth, said method comprising:
    providing to the user a composition comprising an effective amount of dehydroandrosterol and androsterone; and
    inducing physical stress in the user by performing physical exercise.

2. The method of claim 1, wherein the composition further comprises at least one ester, ether, or salt of dehydroandrosterol, or a combination thereof.

3. The method of claim 1, wherein the composition further comprises at least one isomer, stereoisomer, or isostere of dehydroandrosterol, or a combination thereof.

4. The method of claim 1, wherein the composition further comprises a carrier which carries the dehydroandrosterol and androsterone.

5. The method of claim 4, wherein the carrier is selected from the group consisting of a solid, a liquid, and combinations thereof.

6. The method of claim 4, wherein the carrier is shaped and dimensioned to facilitate its oral ingestion.

7. The method of claim 1, wherein the composition is provided to the user at least once every other day.

8. The method of claim 7, wherein the composition is provided to the user daily.

9. The method of claim 8, wherein the composition is provided to the user such that the user is provided between approximately 10 mg and approximately 400 mg daily of dehydroandrosterol.

10. The method of claim 1, wherein the composition further comprises an absorption enhancing agent.

11. The method of claim 10, wherein the absorption enhancing agent is a half-life enhancing agent.

12. The method of claim 1, wherein the relative amount of dehydroandrosterol and androsterone in the composition is between approximately 1:4 and approximately 1:100.

13. The method of claim 1, wherein the composition comprises more than one form of dehydroandrosterol.

* * * * *